United States Patent
Van Esbroeck et al.

(10) Patent No.: US 10,575,925 B2
(45) Date of Patent: Mar. 3, 2020

(54) METHOD AND APPARATUS FOR FORMING AN ORTHODONTIC ALIGNER

(71) Applicant: Structo Pte Ltd, Singapore (SG)

(72) Inventors: Hubertus Theodorus Petrus Van Esbroeck, Singapore (SG); Devansh Sharma, Singapore (SG); Siu Hon Lam, Singapore (SG); Kah Fai Chin, Singapore (SG); Boyle Suwono, Singapore (SG)

(73) Assignee: Structo Pte Ltd, Singapore (SG)

( * ) Notice: Subject to any disclaimer, the term of this patent is extended or adjusted under 35 U.S.C. 154(b) by 0 days.

(21) Appl. No.: 15/603,412

(22) Filed: May 23, 2017

(65) Prior Publication Data

US 2018/0333224 A1 Nov. 22, 2018

Related U.S. Application Data

(60) Provisional application No. 62/509,019, filed on May 19, 2017.

(51) Int. Cl.
  *A61C 7/00* (2006.01)
  *A61C 7/08* (2006.01)
  *A61C 13/00* (2006.01)
  *B29C 51/18* (2006.01)
  *B29L 31/00* (2006.01)

(52) U.S. Cl.
  CPC .............. *A61C 7/002* (2013.01); *A61C 7/08* (2013.01); *A61C 13/0004* (2013.01); *B29C 51/18* (2013.01); *B29C 2791/004* (2013.01); *B29L 2031/753* (2013.01)

(58) Field of Classification Search
  CPC ........... A61C 7/002; A61C 7/08; B29C 51/18; B29C 2791/004
  See application file for complete search history.

(56) References Cited

U.S. PATENT DOCUMENTS

| | | |
|---|---|---|
| 2005/0023710 A1 | 2/2005 | Brodkin et al. |
| 2007/0154518 A1* | 7/2007 | Falotico .................. A61L 27/34 |
| | | 424/424 |
| 2015/0182321 A1 | 7/2015 | Karazivan et al. |
| 2016/0256240 A1* | 9/2016 | Shivapuja ................ A61C 7/08 |
| 2016/0271869 A1* | 9/2016 | Van De Vrie ......... B29C 64/386 |
| 2017/0008333 A1 | 1/2017 | Mason et al. |

FOREIGN PATENT DOCUMENTS

CN 107187025 A 9/2017

OTHER PUBLICATIONS

Foreign Communication from a Related Counterpart Application, International Search Report and Written Opinion dated Jan. 21, 2019, International Application No. PCT/SG2018/050428 filed on Aug. 24, 2018.

\* cited by examiner

*Primary Examiner* — Mathieu D Vargot (57) ABSTRACT

A method of forming an orthodontic aligner from an aligner digital model, the method comprising the steps of:
  (a) three-dimensionally printing an intermediate structure comprising fused filaments from a biocompatible thermoplastic according to the aligner digital model via fused deposition modelling;
  (b) coating the intermediate structure with a biocompatible translucent photopolymer; and
  (c) irradiating the coating with ultraviolet light to cure the coating on the intermediate structure, thereby forming the orthodontic aligner.

10 Claims, 7 Drawing Sheets

METHOD AND APPARATUS FOR FORMING AN ORTHODONTIC ALIGNER

FIELD

This invention relates to a method and apparatus for forming an orthodontic aligner.

BACKGROUND

Orthodontic aligners are commonly used to align teeth for aesthetic reasons. Each aligner must be customized to a patient individually as no two patients have identical teeth alignment. Clear aligners that appear nearly invisible when used are particularly popular among users who prefer discreet treatment and there is a significant demand for them globally. Clear aligners fit over a patient's teeth to apply forces that move the teeth from an original alignment to a desired alignment. In a treatment plan for an individual patient, depending on the amount of movement required, a number of aligners corresponding to different stages of alignment during the course of treatment may be used to move the teeth gradually from their original positions to the desired positions. This is because each aligner is limited in the amount of displacement that it can effect on the teeth.

Currently, to form a number of clear aligners for treatment of a single patient, an impression of the patient's teeth is first taken. The dental impression is scanned to obtain a digital model of the original alignment of the teeth. A treatment plan is then created, comprising a series of teeth digital models of the teeth at different stages of alignment between the original alignment and the desired alignment. A series of dental casts is then made, each corresponding to each of the teeth digital models in the treatment plan. The dental casts are typically made of a photopolymer using stereolithography followed by post-processing in which the dental casts may be washed with ethanol and post-cured with ultraviolet light. A series of aligners are then made from each of the dental casts. The aligners are typically made using thermoforming of a translucent biocompatible thermoplastic sheet onto the dental casts. Subsequently, the thermoformed thermoplastic sheets are removed from the dental casts and trimmed according to the teeth digital models using CNC machining and polished in order to form the aligners, before packaging, labelling and shipping to the patient.

Given the number of aligners required for each patent and the number of patients using such aligners internationally, it would be desirable to reduce the number of steps required to form each aligner to reduce manufacturing time and cost and also greatly reduce the logistical operations in the fabrication process.

SUMMARY

According to a first aspect, there is provided a method of forming an orthodontic aligner from an aligner digital model, the method comprising the steps of:
(a) three-dimensionally printing an intermediate structure comprising fused filaments from a biocompatible thermoplastic according to the aligner digital model via fused deposition modelling;
(b) coating the intermediate structure with a biocompatible translucent photopolymer; and
(c) irradiating the coating with ultraviolet light to cure the coating on the intermediate structure, thereby forming the orthodontic aligner.

The coating in step (b) may comprise dip-coating the intermediate structure in a bath of the biocompatible translucent photopolymer.

According to a second aspect, there is provided an apparatus for forming an orthodontic aligner from an aligner digital model, the apparatus comprising: a three-dimensional printer configured to print an intermediate structure comprising fused filaments from a biocompatible thermoplastic according to the aligner digital model via fused deposition modelling; a coating bath configured to contain the biocompatible translucent photopolymer for dip-coating of the intermediate structure therein; and an ultraviolet light source configured to cure the coating on the intermediate structure to form the orthodontic aligner.

The printer may comprise a print head having a nozzle for dispensing the biocompatible thermoplastic, the nozzle having a width ranging from 0.3 mm to 0.6 mm.

For both the first and second aspects, the biocompatible thermoplastic may be one of: translucent and transparent, and wherein the biocompatible translucent photopolymer is one of translucent and transparent.

According to a third aspect, there is provided a method of forming an orthodontic aligner, the method comprising the steps of:
(a) forming a dental cast corresponding to a teeth digital model;
(b) defining a virtual edge of the aligner corresponding to the teeth digital model wherein the virtual edge and the teeth digital model define a three-dimensional shape of the aligner;
(c) computationally converting the three-dimensional shape into a developed surface having a two-dimensional shape;
(d) cutting the two-dimensional shape from a translucent biocompatible thermoplastic sheet to form a pre-cut aligner sheet; and
(e) thermoforming the pre-cut aligner sheet over the dental cast, thereby forming the orthodontic aligner.

In step (e), a sealing sheet may be used over the pre-cut aligner sheet to create a vacuum seal around the dental cast during the thermoforming.

The sealing sheet may be pliable and of a non-stick material reusable over multiple cycles.

Defining the virtual edge comprises defining a line displaced below a gingival line of the teeth digital model around the teeth digital model.

According to a fourth aspect, there is provided a method of forming an orthodontic aligner from an aligner digital model, the method comprising the steps of:
(a) forming an injection mould having a mould cavity corresponding to the shape of the aligner digital model;
(b) injection moulding a thermoplastic into the injection mould, thereby forming the orthodontic aligner.

Step (a) may comprise forming the injection mould from a photopolymer using stereolithography.

For the first and fourth aspects, the aligner digital model may be developed from a teeth digital model, wherein the teeth digital model is a digital model of a patient's teeth at one of a number of stages of alignment between an original alignment of the patient's teeth and a desired alignment of the patient's teeth.

BRIEF DESCRIPTION OF FIGURES

In order that the invention may be fully understood and readily put into practical effect there shall now be described by way of non-limitative example only exemplary embodiments of the present invention, the description being with reference to the accompanying illustrative drawings.

DETAILED DESCRIPTION

Exemplary embodiments of methods 100, 300, 400 and apparatus 200 of forming an orthodontic aligner will be described below with reference to FIGS. 1 to 13.

Figure 1:
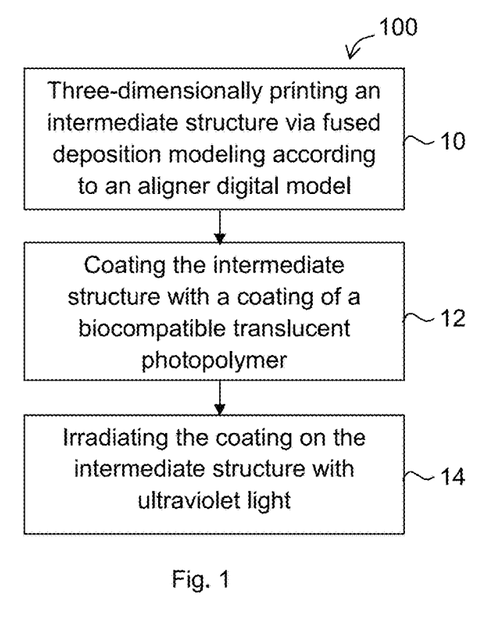
FIG. 1 is a flow chart illustrating a three-dimensional printing and coating process according to an embodiment of the invention.

In a first exemplary method 100 of forming an orthodontic aligner, an intermediate structure 60 is three-dimensionally printed via fused deposition modelling (FDM) according to an aligner digital model (10), in which filaments of a biocompatible thermoplastic are three-dimensionally printed onto each other. The thermoplastic may comprise a grade of polyethylene terephthalate (PET) that is currently used in thermoforming of clear aligners. The thermoplastic is translucent or transparent after forming. The three-dimensional printing step is performed using an apparatus 200 configured to perform FDM.

The aligner digital model is a digital model of the orthodontic aligner that is to be formed in the method 100. The aligner digital model is developed from a teeth digital model using currently available software and techniques. The teeth digital model is a digital model of the patient's teeth at one of a number of stages of alignment between an original alignment of the patient's teeth (before treatment) and a desired alignment of the patient's teeth (after treatment with one or more aligners). The teeth digital model is part of a treatment plan for the patient and is developed from a digital model of the original alignment of the patient's teeth using current methods. The digital model of the original alignment of the teeth may be obtained by methods such as scanning a dental impression of the patient or scanning the patient intra-orally using currently known methods.

Figure 5:
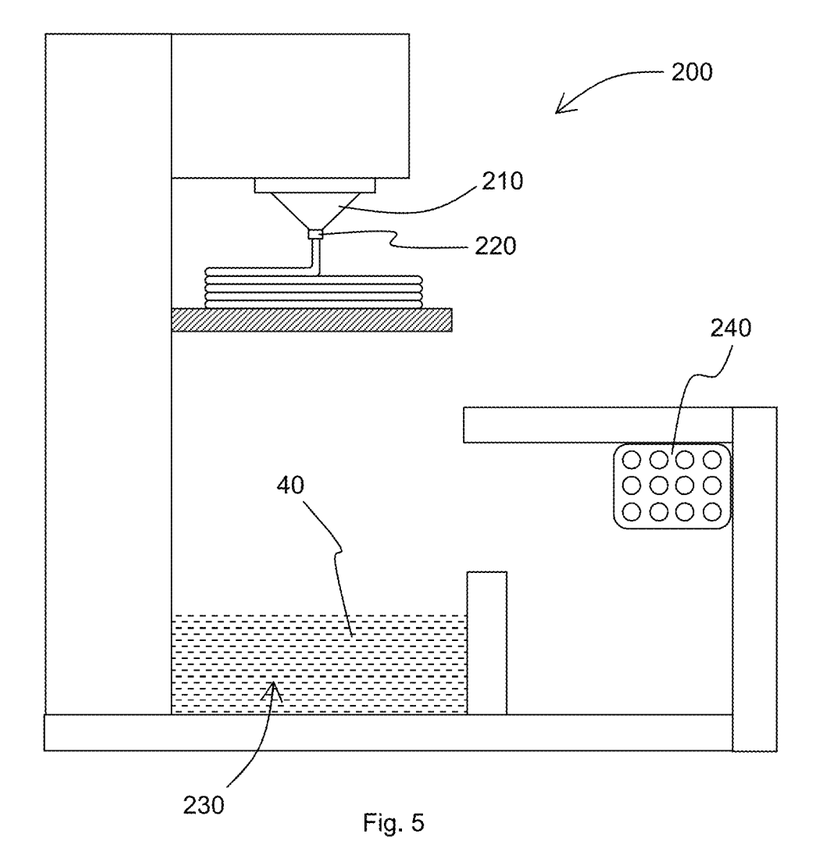
FIG. 5 is a schematic illustration of an apparatus for forming the orthodontic aligner.

The printed intermediate structure 60 comprising fused filaments 30 is generally of the shape of the aligner digital model. Each printed filament 30 preferably has a width corresponding to a wall thickness of the aligner to be formed, so that the wall thickness of the aligner may be printed in a single pass of a printer head 210 of the apparatus 200. Accordingly, a nozzle 220 of the printer head 210 that dispenses the biocompatible thermoplastic may have a nozzle width ranging from 0.3 to 0.6 mm, preferably 0.4 to 0.5 mm.

Figure 2A:
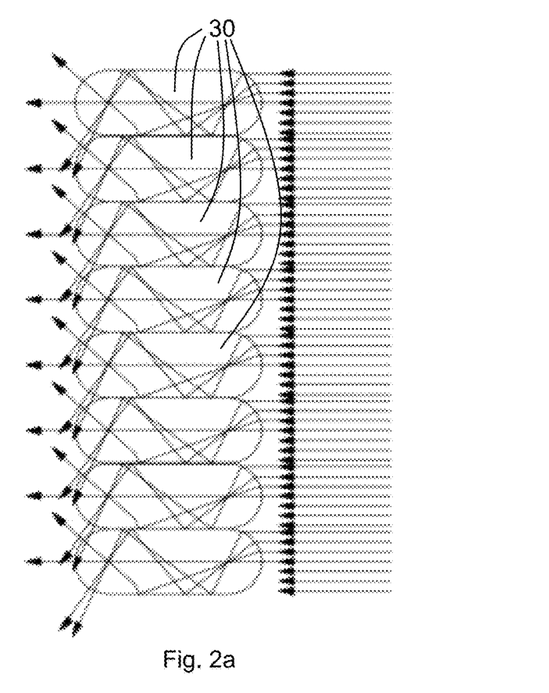
FIG. 2a is a schematic illustration of light passage through printed filaments of transparent thermoplastic having oblong cross-sections.
Figure 2B:
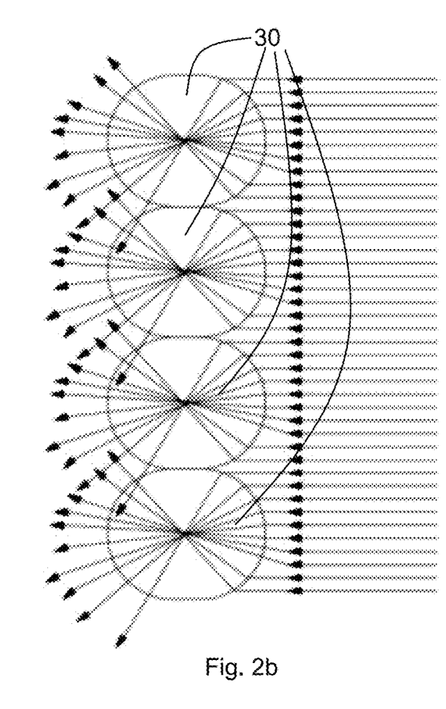
FIG. 2b is a schematic illustration of light passage through printed filaments of transparent thermoplastic having nearly circular cross-sections.
Figure 3:
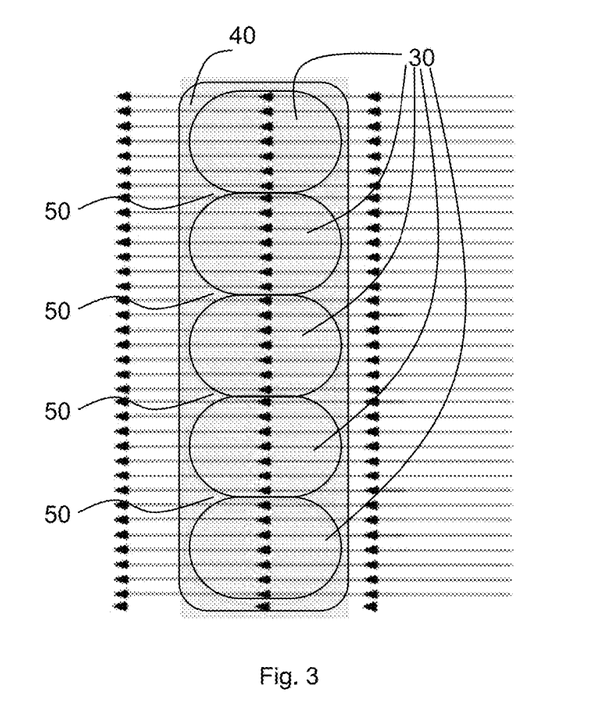
FIG. 3 is a schematic illustration of light passage through printed filaments of transparent thermoplastic after application of a coating of a biocompatible translucent photopolymer.

The printed intermediate structure 60 lacks optical clarity because the fused filaments 30 each have a curved cross-sectional profile, typically comprising a cylindrical or oblong cross-section that refract and diffuse light, as shown in FIGS. 2a and 2b. To achieve translucency in the formed aligner, the intermediate structure 60 is coated with a coating 40 of a biocompatible translucent photopolymer 40 (12) that is translucent or transparent after forming. An example of the biocompatible translucent photopolymer 40 that may be used as a coating 40 is Model Ortho produced by NextDent®. The coating 40 fills in the spaces 50 between adjacent filaments 30 of the intermediate structure 60, as shown in FIG. 3, thereby smoothening out the surface of the intermediate structure 60.

Figure 6:
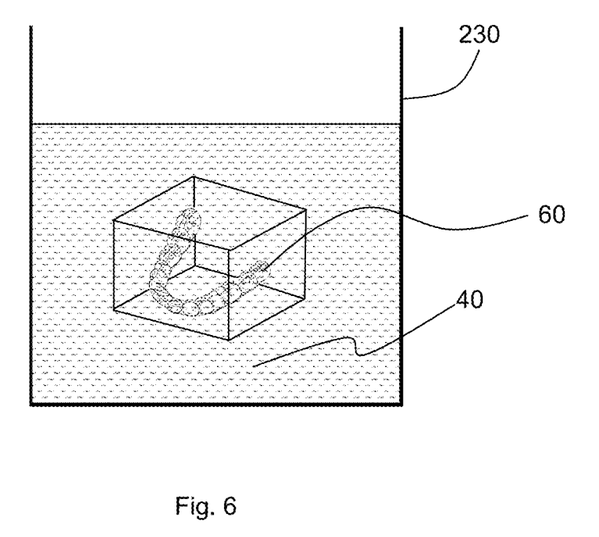
FIG. 6 is a schematic illustration of applying the coating of biocompatible translucent photopolymer by dip coating.
Figure 7:
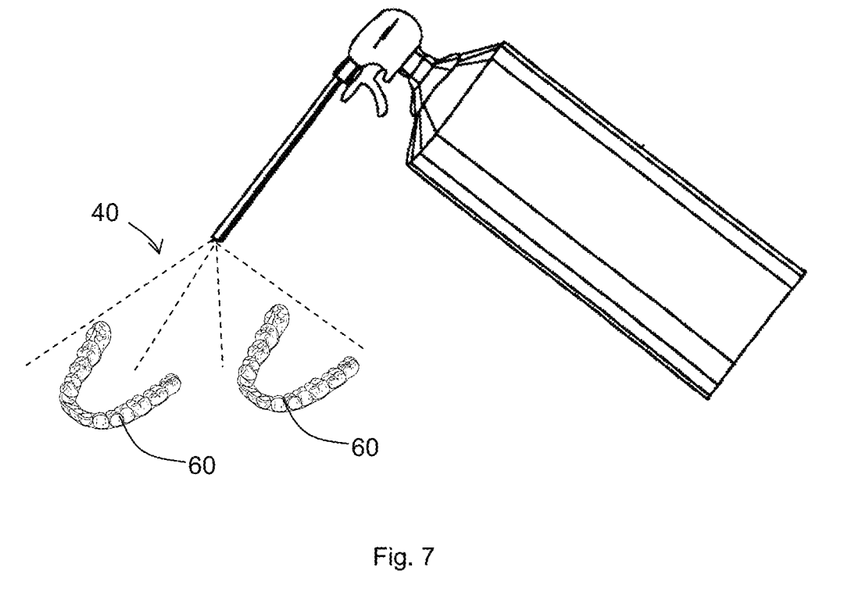
FIG. 7 is a schematic illustration of applying the coating of biocompatible translucent photopolymer by spray coating.

The apparatus 200 as shown in FIG. 5 is configured to perform coating of the intermediate structure 60, and may comprise a coating bath 230 configured to contain the biocompatible translucent photopolymer 40. The apparatus 200 may be configured to automatically perform dip-coating of the intermediate structure 60 in the bath 230 of translucent photopolymer 40 after printing the intermediate structure 60, as shown in FIG. 6. Alternatively, the intermediate structure 60 may be spray coated with the biocompatible translucent photopolymer 40 as shown in FIG. 7. One or more units of the intermediate structure 60 may be coated at the same time, whether by dip coating or spray coating.

Figure 4:
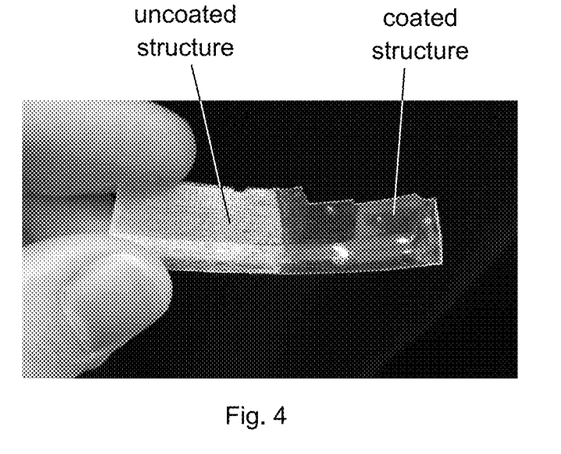
FIG. 4 is a photograph of a structure of printed filaments partially coated with the biocompatible translucent photopolymer.

The coating 40 on the intermediate structure 60 is subsequently irradiated with ultraviolet light (14), to cure the coating 40. The apparatus 200 preferably comprises an ultraviolet light source 240 configured to perform the ultraviolet light irradiation. After UV curing, the formed aligner is translucent or transparent, as shown in FIGS. 3 and 4, as a result of the coating 40 forming a smooth surface over the printed filaments 30 of the intermediate structure 60 that reduces refraction and diffusion of light.

Using the method 100 and apparatus 200 described above, orthodontic aligners may be expeditiously formed directly from aligner digital models, without requiring the fabrication of dental casts in order to thermoform the aligners on the dental casts. In this way, manufacturing cost and time can be drastically reduced since stereolithographic forming of dental casts from the aligner digital models is no longer required.

A major advantage of the presently disclosed method 100 and apparatus 200 is that they allow the orthodontic aligner to be designed for greater clinical efficacy, as different parts of the orthodontic aligner can be formed to have different thicknesses using the method 100 and apparatus 200. For example, certain areas may be formed to be thicker to apply more pressure or improve stiffness at those areas, while other areas may be made thinner and more flexible. This can be customised to individual patient requirements, for example, to move the front teeth by forming the front part of the aligner to be stiffer and thicker, while leaving the molars stationary with the aligner being thinner and therefore more comfortable where it covers the molars. Such advantageous variable thickness in a single orthodontic aligner cannot be obtained using current processes where thickness of the aligner is uniform throughout, the thickness being equal to that of the sheet of plastic that is currently thermoformed over the dental cast.

Pre-Cut Aligner Sheet

A second exemplary method 300 (FIG. 12) of forming orthodontic aligners over the currently used thermoforming method is also disclosed. The improved method comprises first taking an impression of the patient's teeth and scanning the dental impression to obtain a digital model of the original alignment of the teeth. A treatment plan is then created, comprising a series of teeth digital models of the teeth at different stages of alignment between the original alignment and a desired alignment. A series of dental casts is made, each corresponding to each of the teeth digital models in the treatment plan (301). The dental casts are typically made of a photopolymer using stereolithography followed by post-processing in which the dental casts may be washed with ethanol and post-cured with ultraviolet light.

Figure 12:
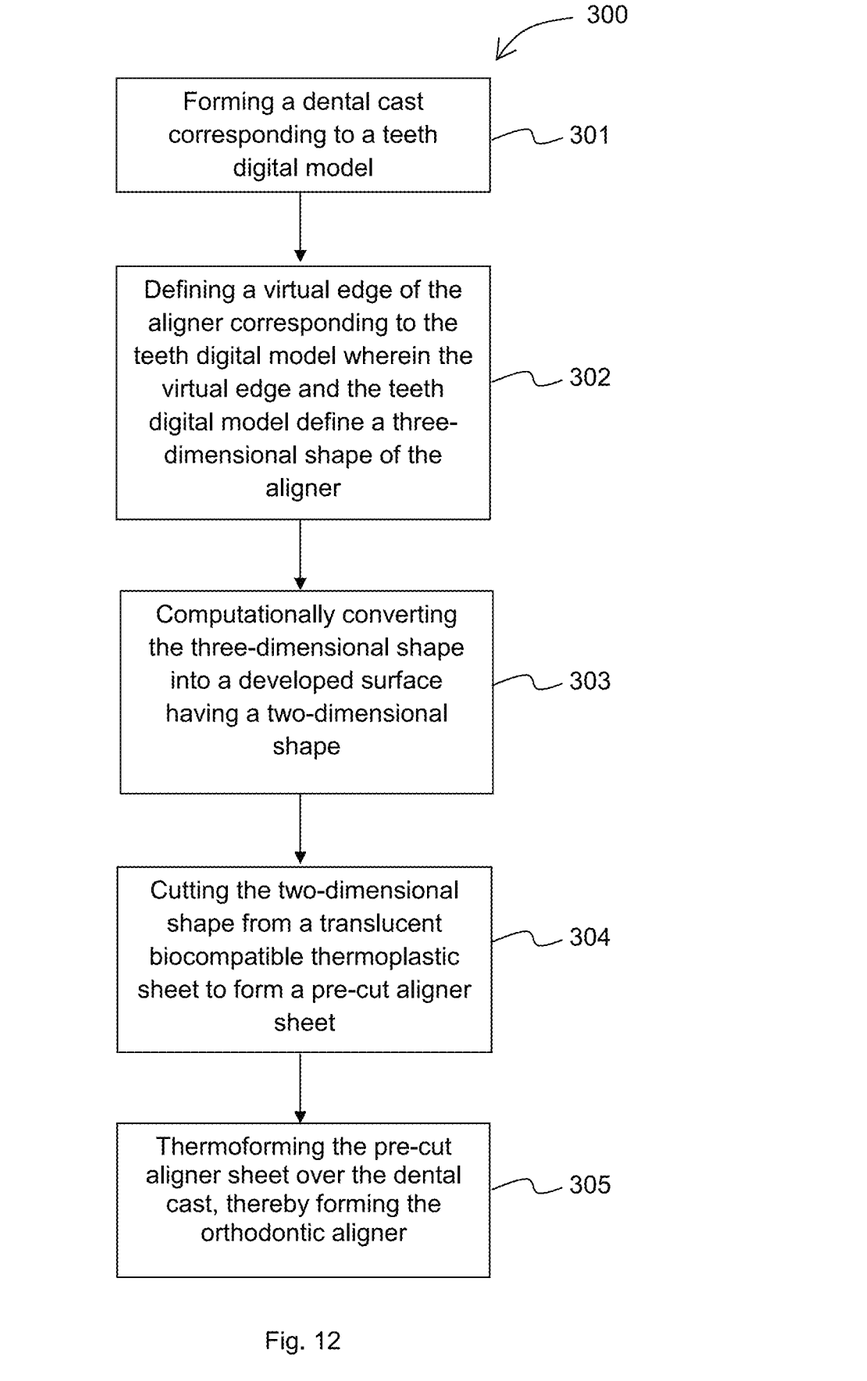
FIG. 12 is a flowchart of a second exemplary method of forming an orthodontic aligner.

For each of the teeth digital models, a virtual edge of a three-dimensional (3D) aligner corresponding to each of the teeth digital models can be defined. This can be done by defining a line that is displaced below a gingival line of the teeth digital model around the teeth digital model. The displacement may be 2 mm or as otherwise desired. The virtual edge and teeth digital model above the virtual edge thus define a 3D shape of the aligner (302). The 3D shape is computationally converted into a developed surface having a two-dimensional (2D) shape (303). This may be performed using an appropriate surface development algorithm that maps the virtual edge into a perimeter of a 2D developed surface.

Figure 8:
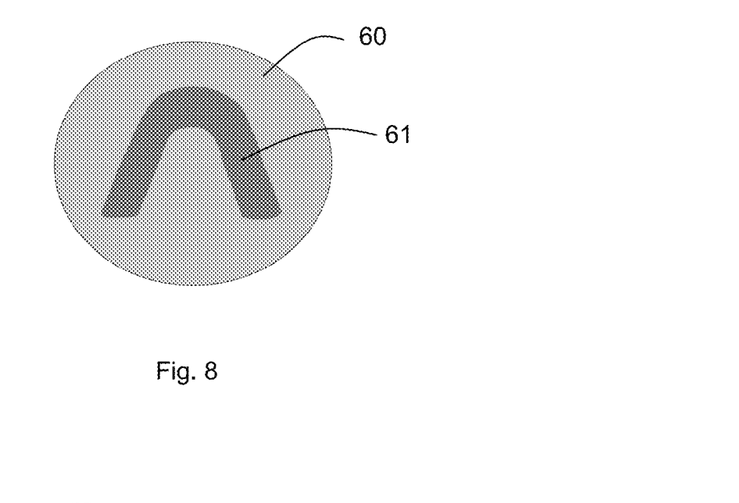
FIG. 8 is a schematic illustration of a pre-cut aligner sheet.
Figure 9:
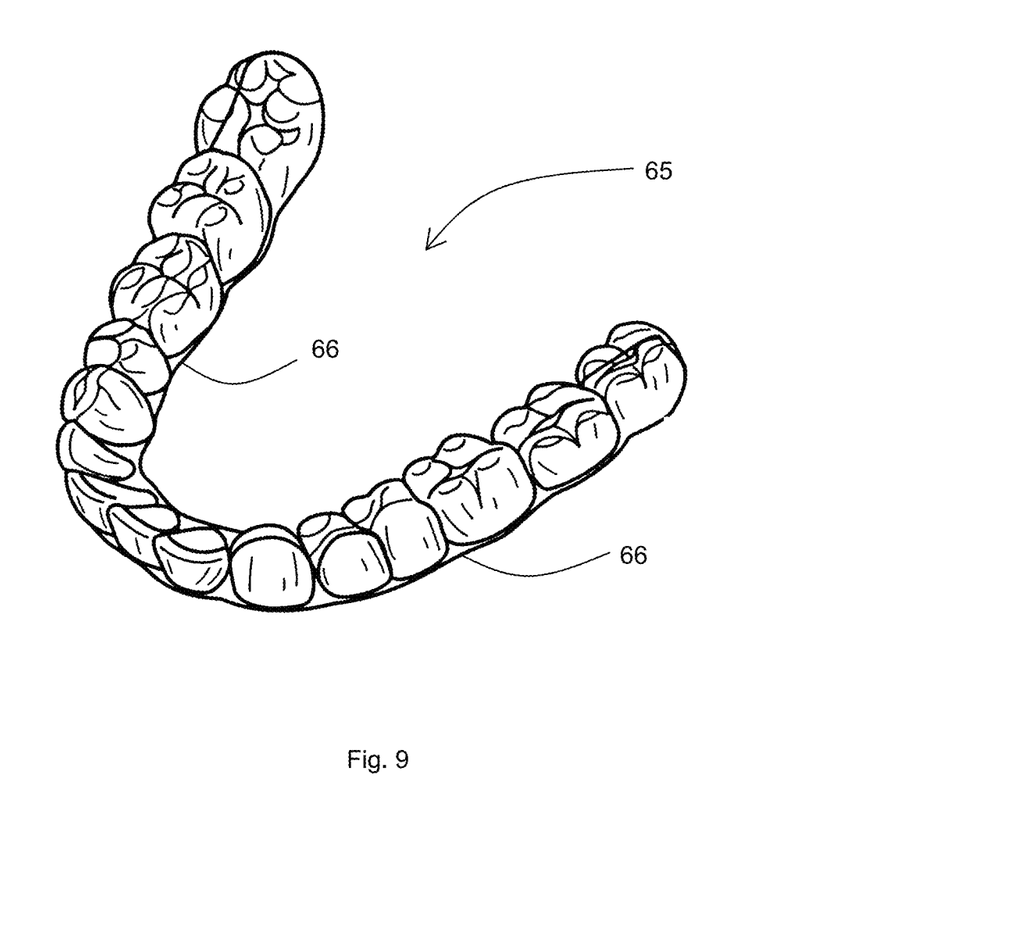
FIG. 9 is an illustration of a thermoformed 3D aligner having an aligner edge requiring no trimming.
Figure 10:
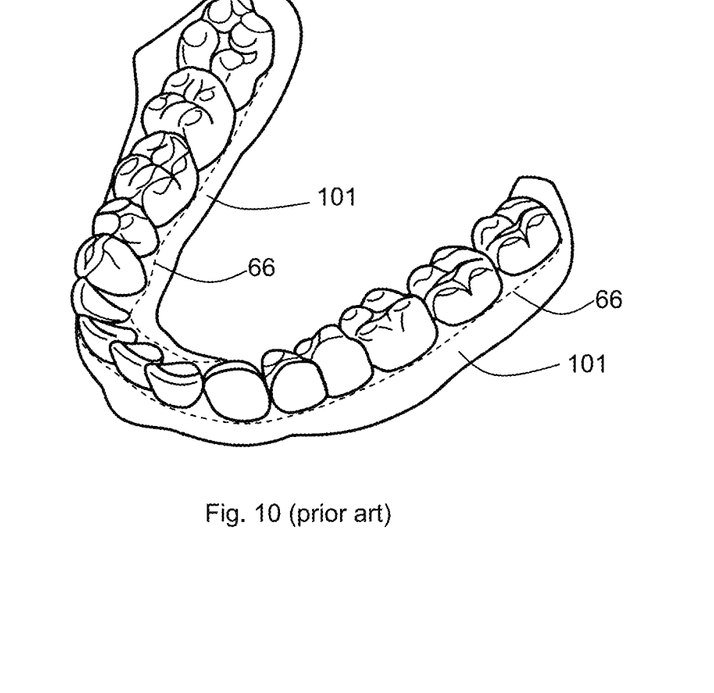
FIG. 10 (prior art) is an illustration of a thermoformed 3D aligner having an aligner edge that requires trimming.

The 2D shape is then cut from a translucent biocompatible thermoplastic sheet 60 to form a pre-cut aligner sheet 61, as shown in FIG. 8 (304). When the pre-cut aligner sheet 61 is thermoformed over the dental cast of the corresponding teeth digital model, the 3D aligner 65 is formed (305) having an aligner edge 66 as shown in FIG. 9 that corresponds to the virtual edge defined using the teeth digital model, as described above. This eliminates the need for a further trimming step to be performed on the thermoformed aligner 65 as no excess material extends beyond the desired aligner edge 66. On the contrary, in the current method where a thermoplastic sheet that is significantly larger than the aligner is thermoformed over the dental cast, trimming away of the excess material 101 that extends beyond the desired aligner edge 66 as shown in FIG. 10 is needed in order to form the actual aligner. In this way, the improved method removes the trimming step from the current aligner forming method, thus saving time and cost.

Figure 11:
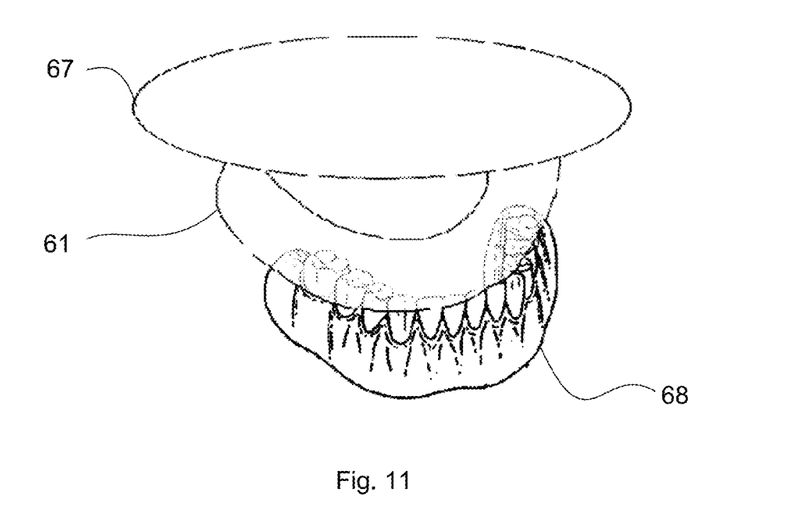
FIG. 11 is a schematic illustration of thermoforming a pre-cut aligner sheet over a dental cast using a sealing sheet.

To effectively thermoform the pre-cut aligner sheet 61 over the dental cast, a sealing sheet 67 may be used over the pre-cut aligner sheet 61 to create the vacuum seal around the dental cast 68, as shown in FIG. 11. During thermoforming, the pre-cut aligner sheet 61 is first held in place under the sealing sheet 67 and over the dental cast 68. The sealing sheet 67 with the pre-cut aligner sheet 61 is then pulled down over the dental cast 68 using the vacuum pressure in order for the pre-cut aligner sheet 61 to take the shape of the dental cast 68 under heat. The sealing sheet 67 is preferably pliable and of a non-stick material in order to be readily released from the thermoformed aligner 65 and reusable over many cycles.

Injection Moulding

Figure 13:
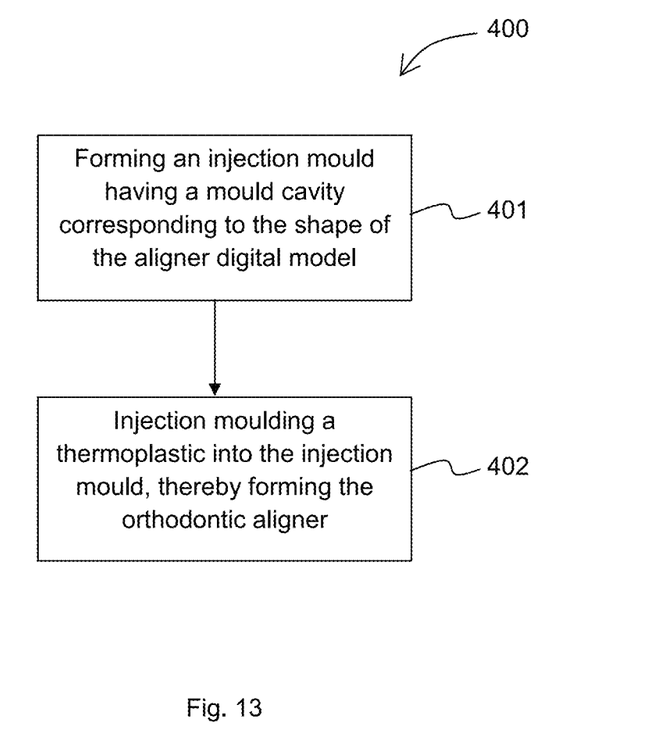
FIG. 13 is a flowchart of a third exemplary method of forming an orthodontic aligner.

A third exemplary method 400 of forming orthodontic aligners is disclosed, as shown in FIG. 13. The alternative method comprises first taking an impression of the patient's teeth and scanning the dental impression to obtain a digital model of the original alignment of the teeth. A treatment plan is then created, comprising a series of teeth digital models of the teeth at different stages of alignment between the original alignment and a desired alignment. For each teeth digital model, a corresponding aligner digital model is developed for the treatment plan.

A series of injection moulds is then made, each injection mould comprising a mould cavity corresponding to the shape of an aligner digital model in the treatment plan (401). Each injection moulds is preferably made from a photopolymer using stereolithography followed by post-processing by washing with ethanol and post-curing with ultraviolet light.

Using the injection moulds, conventional injection moulding may be performed to obtain injection-moulded aligners (402). Appreciably, one injection mould may comprise a single block having a number of aligner-shaped cavities therein, so that a single injection moulding shot can produce a number of aligners at once.

Whilst there has been described in the foregoing description exemplary embodiments of the present invention, it will be understood by those skilled in the technology concerned that many variations and combination in details of design, construction and/or operation may be made without departing from the present invention. For example, while PET has been mentioned above as a possible biocompatible thermoplastic to be used, other options for the biocompatible polymer include nylon and polylactic acid (PLA).

The invention claimed is:

1. A method of forming an orthodontic aligner from an aligner digital model, the method comprising the steps of:
   (a) three-dimensionally printing an intermediate structure comprising fused filaments from a biocompatible thermoplastic according to the aligner digital model via fused deposition modelling in which the filaments are three-dimensionally printed onto each other, each filament having a width corresponding to a wall thickness of the orthodontic aligner and printed such that a wall thickness of the orthodontic aligner is printed in a single pass;
   (b) coating the intermediate structure with a biocompatible translucent photopolymer; and
   (c) irradiating the coating with ultraviolet light to cure the coating on the intermediate structure, thereby forming the orthodontic aligner.

2. The method of claim 1, wherein the biocompatible thermoplastic is one of translucent and transparent after forming the orthodontic aligner, and wherein the biocompatible translucent photopolymer is one of translucent and transparent after forming the orthodontic aligner.

3. The method of claim 1, wherein the aligner digital model is developed from a teeth digital model, wherein the teeth digital model is a digital model of a patient's teeth at one of a number of stages of alignment between an original alignment of the patient's teeth and a desired alignment of the patient's teeth.

4. The method of claim 1, wherein the coating in step (b) comprises dip-coating the intermediate structure in a bath of the biocompatible translucent photopolymer.

5. The method of claim 1, wherein three-dimensionally printing the intermediate structure comprises using a three-dimensional printer.

6. The method of claim 5, wherein the printer comprises a print head having a nozzle for dispensing the biocompatible thermoplastic.

7. The method of claim 6, wherein the nozzle has a width ranging from 0.3 mm to 0.6 mm.

8. The method of claim 6, wherein the nozzle has a width ranging from 0.4 mm to 0.5 mm.

9. The method of claim 1, wherein the biocompatible thermoplastic comprises a grade of polyethylene terephthalate (PET).

10. The method of claim 1, wherein coating the intermediate structure with the biocompatible translucent photopolymer comprises:

filling in spaces between the fused filaments with the biocompatible translucent photopolymer; and creating a smooth surface of the intermediate structure based on filling in the spaces.

\* \* \* \* \*